United States Patent [19]
Strobel et al.

[11] Patent Number: 5,721,229
[45] Date of Patent: Feb. 24, 1998

[54] SOLUBLE FORMS OF CEPHALOSPORINS AND TREATMENT OF ANIMALS

[75] Inventors: Michael A. Strobel, Northfield; Pat Soderlund, New Prague, both of Minn.

[73] Assignee: Veterinary Pharmacy Corporation, Northfield, Minn.

[21] Appl. No.: 578,824

[22] Filed: Dec. 26, 1995

[51] Int. Cl.$^6$ ............................................. A61K 31/545
[52] U.S. Cl. ........................ 514/209; 514/200; 514/202; 514/206
[58] Field of Search ............................. 514/200, 202, 514/206, 209

[56] References Cited

U.S. PATENT DOCUMENTS

| | | | |
|---|---|---|---|
| 3,719,758 | 3/1973 | Jordan | 424/246 |
| 3,940,483 | 2/1976 | Dursch | 514/209 |
| 4,600,773 | 7/1986 | Engel et al. | 544/30 |
| 4,726,951 | 2/1988 | Panoz | 424/465 |
| 5,254,545 | 10/1993 | Ishibashi et al. | 514/202 |

*Primary Examiner*—Rebecca Cook

[57] ABSTRACT

A dry solid mixture of a hydroxypolycarboxylic acid and a cephalosporin where the hydroxypolycarboxylic acid of the formula

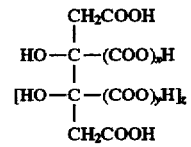

where x and y are 0 or 1 and z is 0 to 3, in the weight ration of hydroxypolycarboxylic acid to cephalosporin of at least 1.8. The invention comprises a solution made from the dry solid mixture and a process of treating animals with cephalosporin by including the solution in the water fed to the animals so that the animals can ingest the cephalosporin. A particularly preferred mixture is one of citric acid and cephalexin.

106 Claims, No Drawings

SOLUBLE FORMS OF CEPHALOSPORINS AND TREATMENT OF ANIMALS

BRIEF DESCRIPTION OF THE INVENTION

A readily water-soluble ingestible form of cephalosporins (e.g., cephalexin, cephalothin, and cephaloridine) formed by their reaction with a hydroxylatedpolycarboxylic acid of the formula

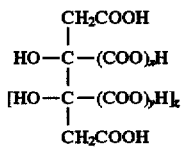

where x and y are 0 or 1 and z is 0 to 3. This water-soluble form possesses palatability and unique storage stability. The water-soluble form of the invention allows feeding orally to animals, as well as humans, without loss of antibiotic benefits. This water-soluble form is derived from an anhydrous solid, particulate mixture of the cephalosporin and the hydroxylatedpolycarboxylic acid.

BACKGROUND OF THE INVENTION

Cephalosporins comprise the class of amphoteric antibiotics of the group of broad-spectrum, relatively penicillinase-resistant antibiotics derived from the fungus Cephalosporium, which share the nucleus 7-aminocephalosporanic acid. They are related to the penicillins in both structure and mode of action. Their antibacterial activity results from inhibition of the cross-linking of peptidoglycan units in the cell wall. The cephalosporins available for medicinal use are semisynthetic derivatives of the natural antibiotic cephalosporin C. The cephamycins cefotetan and cefoxitin and the β-lactam moxalactam are included with the cephalosporins because of their dose relationship to them. Cephalosporin C is isolated from *Cephalosporium acremonium*, which is the parent compound of a number of semisynthetic antibiotics, including cefazolin sodium, cephalexin (α-aminobenzyl-3-desacetoxycephalosporin), cephaloridine, cephaloglycin, cephalothin, cephapirin and cephradine (α-amino-2,5-dihydrobenzyl-3-desacetoxycephalosporin), used in the treatment of a wide variety of infections due to sensitive gram-positive and gram-negative bacteria. The first generation cephalosporins have a broad range of activity against gram-positive organisms and a narrow range of activity against gram-negative organisms and include cephalothin, cefazolin, cephaloridione, cephapirin, cephadrine, cephalexin, and cefadroxil. The second generation cephalosporins are more active against gram-negative organisms and less active against gram-positive organisms than the first-generation agents. They include cefamanadole, cefoxitin, cefaclor, and cefurotrime. The third-generation cephalosporins are a group of β-lactamase-resistant cephalosporins that are more active against gram-negative organisms and less active against gram-positive organisms than second-generation agents. They include cefoperazone, cefotaxime, ceftriaxone, ceftazidime, ceftizoxime, and moxalactam. Collectively, all fall under the label of cephalosporin, and as that term is used herein and in the claims, the term covers any one or more of these various generation agents.

Cephalexin is a widely employed antibiotic. It is effective against a wide range of gram-negative and gram-positive bacteria. It is used in the treatment of infections of the urinary and respiratory tracts and of skin and soft tissues due to sensitive pathogens. In treating humans, it is typically administered orally, e.g., in a tablet form.

The treatment of animals with a cephalosporin such as cephalexin is fraught with many difficulties. For example, injecting cephalexin is time consuming and costly, especially when large numbers of animals are involved. It is also potentially hazardous to the animal because a needle can break off in the animal and/or create an infective injection site. Feeding even a farmyard animal, let alone a wildlife species, with a cephalexin tablet is minimally a taxing chore. Mixing solid particles of cephalexin in the animal's food assures uneven dosage of the medication and, because cephalexin is unpalatable, creates a bad tasting mixture that the animal is less likely to ingest. Because cephalexin is water insoluble, it cannot be supplied with the animals' water supply. However, when cephalexin is made water soluble by derivatization according to the prior art, its aqueous solutions typically suffer from poor shelf-life stability, sometimes having a shelf-life of only a few hours, and unpalatability, causing the animals to reduce their ingestion of water containing the unpalatable form of cephalexin.

Cephalexin readily dissolves in the acidic environment of the normal stomach, e.g., pH of less than 3.0. It is available in the form of suspensions and tablets (such as cephalexin monohydrate), an unstable water-soluble form of sodium cephalexin that is stable for less than about 6 hours, and a water soluble form of cephalexin hydrochloride (such as cephalexin hydrochloride monohydrate, see U.S. Pat. Nos. 4,600,773 and 4,775,751) that is sold in coated tablet form (Keftab® from Eli Lilly and Company). Aqueous solutions of sodium cephalexin and cephalexin hydrochloride are unpalatable. Such unpalatable forms of cephalexin have been added to animal feed as a method of treating the animals. One notes a noticeable drop-off in the feeding rate of animals fed cephalexin in that manner clearly indicating that the animal is unsatisfied with the taste of these forms of the drug.

Cephalexin hydrochloride and cephalexin monohydrate are readily dissolved in forms which are 50% positively charged and 50% neutrally charged. The neutrally charged form has limited solubility compared to the ionized drug forms. At a pH 4.5, cephalexin monohydrate exists as 100% neutrally charged particles, with limited solubility. However, cephalexin hydrochloride would be expected to be more soluble because of the hydrochloride moiety.

Jordan, U.S. Pat. No. 3,719,758, patented Mar. 6, 1973, describes a method of promoting the growth and improving the efficiency in poultry and swine by administering orally to them an effective amount of cephalosporin C [7-(5'-aminoadipamido) cephalosporanic acid]. Cephalosporin C can be employed as the free acid or as the salt. Salts can be formed with either "inorganic or organic acids, as for example, hydrochloric, hydrobromic, sulfuric, phosphoric, acetic, propionic, citric, oxalic, maleic, malic, succinic, tartaric, toluenesulfonic, naphthalene-sulfonic and like acids." According to Jordan, "[B]ecause of their greater water solubility, ease of preparation, and amenability to incorporation into various medicated feeds, the use of the sodium, potassium and amine salts of cephalosporin C is preferred in the practice of this invention." All of the examples of the patent describe the use of sodium cephalosporin C, which in effect is a statement that excess salt forming agent is not present in the sodium cephalosporin C. The patent fails to set forth the stoichiometry of the salt forming agent present in making the cephalosporin C salts or deal with the palatability issue.

Dursch, U.S. Pat. No. 3,940,483, patented Feb. 24, 1976, describes dry solid antibiotic compositions of a solid acidic, basic or amphoteric antibiotic, inclusive of cephalosporin, such as cephalexin, and a suitable solid basic or acidic additive, for reconstitution as injectables upon addition of water. According to this patent, antibiotics of limited water solubility are formulated for parenteral application either as aqueous suspensions, or by preparing water soluble derivatives (e.g., salts, esters or complexes) of the parent compound, which upon parenteral administration are either in equilibrium with the parent compound, or which are transformed back into the parent compound in the patient's system. The patentee states that a solids in suspension "severely limits the mode of parenteral administration." The patentee also states that the pharmaceutically acceptable solid derivatives are frequently prepared with significant yield losses. The derivatives are alleged to resist isolation in suitable form altogether. The patentee overcomes the prior art deficiencies by premixing antibiotics of limited water solubility which are either acidic, basic, or amphoteric in nature, with a suitable solid additive to form a dry mixture. On addition of water to the dry mixture, physiologically acceptable solutions of water soluble salts of the antibiotic are formed in situ and can be administered without delay. The patentee illustrates antibiotics such as penicillins, e.g., ampicillin, cephalosporins, e.g., cephalexin, and the like, as amphoteric antibiotics that can be dry blended. According to this patent, "suitable additives for amphoteric antibiotics may be of either acidic or basic character."Illustrative of suitable acidic additives are alkali metal hydrogen sulfates, and organic acids like citric acid, tartaric acid or maleic acid. There is no explicit indication of the amount of acid compound that is to be used in the dry mixture. In this regard, the patentee states: "The selected solid additive is usually employed in an amount just sufficient to assure complete dissolution of the antibiotic upon addition of a small volume of water. This amount may well be less than the stoichiometric quantity required for complete conversion to a salt. Herein lies another advantage of the present invention over the use of pre-formed salts; frequently, less extreme conditions of acidity or basicity are required for complete dissolution and superior stability of such solutions can be expected. For example, 95 mole-% of sodium carbonate is sufficient to dissolve ampicillin at pH 8.3, whereas an aqueous solution of pre-formed sodium ampicillin shows about pH 9.5." The examples of the patent show dry mixtures that on dissolution in water result in pH's as low as 2 and as high as 9.7. The patent is unconcerned with ingestion of the antibiotic or for forming a palatable dry mixture that can be ingested by the animal.

La Via et al., U.S. Pat. No. 4,235,900, combine arginine and cephradine to form a solid mixture that is soluble in water. This forms an injectable solution.

French patent publication 2 308 368 describes a lysine salt of cephalexin that can be administered orally as well as by intramuscular or intravenous injection. Such a lysine salt dissolved in water has been found to be unpalatable.

There is a need for stable liquid forms of cephalosporins, especially cephalexin, that can be orally administered (i.e., ingested) via an animal's drinking water without rejection by the animal because of the bad taste imparted by the liquid cephalosporin. Such a palatable form of cephalosporins, especially the widely used cephalexin, lows large scale dosage-controlled treatment of animals with the antibiotic. An unpalatable soluble form of cephalexin affects the taste of the drinking water to a degree that jeopardizes the amount of cephalexin ingested by the animal thus making it impossible to accurately control dosage to the animal.

THE INVENTION

This invention relates to the formation of solid mixtures and aqueous solutions of cephalosporin antibacterial agents with a material that aids in its dissolution in water to render it ingestive and palatable. The cephalosporins used in the practice of this invention are those that are antibacterials to the bacteria in the animal that is being treated. The term "anhydrous," when used to characterize the solid mixture of the cephalosporin, does not exclude bound water in the form of hydrated water bound to the cephalosporin. For the purposes of this invention, even when a cephalosporin hydrate such as cephalexin monohydrate is provided in the mixture, the mixture is still regarded to be anhydrous. The reason for this characterization is based on the fact that the hydrate form of the cephalosporin remains solid and dry and can be formed into the mixture without forming a solution.

The solid essentially anhydrous mixture contains a cephalosporin and a hydroxypolycarboxylic acid of the formula

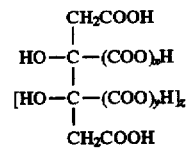

where x and y are 0 or 3 and z is 0 to 3, in appropriate amounts so that upon addition to water, there is an apparent reaction to form a palatable soluble "hydroxyacylated cephalosporin," that is, a water soluble salt of the cephalosporin and the hydroxypolycarboxylic acid. Suitable hydroxylatedpolycarboxylic acids include 2-hydroxy n-propyl 1,2,3-tricarboxylic acid (also known as citric acid), 2,3-diydroxyl n-butyl 1,4-dicarboxylic acid (also known as tartaric acid), 2-hydroxyl n-propyl 1,3-dicarboxyl acid (also known as 2-hydroxy malonic acid), 2-hydroxyl n-butyl 1,2,4-tricarboxylic acid, 2-hydroxy n-butyl 1,3,4-tricarboxylic acid, glucaric acid, and the like.

An important facet of the invention is the weight ratio of hydroxypolycarboxylic acid to the cephalosporin in the mixture. It has been determined that the weight ratio of anhydrous solid hydroxypolycarboxylic acid to solid cephalosporin (typically in the hydrate form) should be at least about 1.8 to 1, preferably at least 2.5 to 1, most desirably about 3 to 1, in the mixture in order to readily form, in combination with tap, deionized or distilled water, a palatable solution that can be fed to animals without rejection. The highest weight ratio of hydroxypolycarboxylic acid to cephalosporin may be about 10 to 1, though it is preferred to keep the weight ratio below about 5 to 1 of hydroxypolycarboxylic acid to cephalosporin. At a lower weight ratio, the resultant cephalosporin and hydroxypolycarboxylic acid mixture does not form a stable solution, and in many cases, will not form a solution. In all cases tested, when attempting to form a solution from a hydroxypolycarboxylic acid/ cephalosporin mixture having a weight ratio less than 1.8, to the extent a solution is formed, the solution is clearly unpalatable.

In addition, in order to form a palatable aqueous solution of the hydroxyacylated cephalosporin, the hydroxyacylated cephalosporin solution has a pH of about 3.0 to as high as about 4.0, preferably from about 3.3 to about 3.8.

To enhance the palatability of the solution, one may add flavorings and/or artificial sweeteners such as cyclohexylsulfamic acid, saccharin (o-benzosulfimide), and Aspartame (i.e., L-Aspartyl-L-phenylalanine methyl ester) sold as Nutrasweet® artificial sweetener, and the like, in small amounts that are sufficient to enhance the palatability of the hydroxyacylated cephalosporin solution. If the animals would not be adversely affected by inclusion of sugar in the formulation, then sugar can be used to sweeten the solution. In actual practice, the sweetener and the flavoring are added in amounts that overcome the natural bad taste of the cephalosporins that is not fully mitigated by the presence of the hydroxypolycarboxylic acid. It has been determined that pigs favor strawberry and licorice flavorings.

The invention can be employed to treat all forms of domestic animals, such as livestock, e.g., pigs (including swine), beef and dairy cattle, horses, poultry (especially chickens and turkeys), sheep, and dogs, cats, and the like, as well as non-domestic animals such as deer, buffalo, and the like, that are kept in herds and fed from a controlled water supply. Cephalexin, as an example, is normally 90% absorbed by the body when ingested.

The dosage of the anhydrous mixture used in forming an aqueous solution of cephalosporin and hydroxylatedpolycarboxylic acid for feeding to the animals is quite broad, and should be sufficient to provide the required amount of cephalosporins prescribed by the veterinarian. As a rule, the amount of the anhydrous preparation of cephalosporin and hydroxylatedpolycarboxylic acid that is dissolved into water for feeding the animals should provide about 2 to about 15, preferably from about 5 to about 10, milligrams of the cephalosporin for each pound of weight of the animals being treated.

The invention allows for the preparation of dry anhydrous mixtures of the cephalosporins and the hydroxypolycarboxylic acid in the weight ratio of 1.8 to 5.0 of the hydroxypolycarboxylic acid to 1 of the cephalosporin. The mixture may contain from about 0.1 to about 5 weight percent of a flavoring and from about 0.1 to about 10 weight percent of an artificial sweetener. In special situations, greater and smaller amounts of the hydroxypolycarboxylic acid, flavoring and artificial sweetener can be used to advantage to achieve the objectives of this invention. The anhydrous mixture is stable and can be kept for an infinite period of time without deterioration. Contrary to the normal attributes of prior art acidic solutions of cephalosporins, the solutions of the invention, made by dissolving the cephalosporin and the hydroxypolycarboxylic acid in water, have remarkable storage stability as compared to non-acidified cephalosporins such a cephalexin monohydrate, and the like. These solution can be kept for as long as 14 days, at refrigeration conditions of about 7° C., without deterioration or separation (e.g., precipitation of cephalosporin).

The mixing of the solid particulate cephalosporin and the solid particulate hydroxypolycarboxylic acid, with or without flavoring and sweetener, is not difficult to achieve. Any method and equipment that is effective in making a powdered mixture can be used in the practice of this invention to produce the anhydrous powder mixture of the cephalosporin and the hydroxylatedpolycarboxylic acid. For example, small packets of the mixture can be put into a plastic bag, typically one made of polyethylene, or polyvinyl chloride-vinylidene chloride copolymer or Mylar® (a film form of polyethyleneterephthalate), and the like. The mixtures can be made in such bags by separately feeding solid particulate cephalosporin and solid particulate hydroxylatedpolycarboxylic acid. Then the ingredients in the bag can be worked by hand to mix the particulates into an essentially homogeneously distributed mixture. The particulates can be mixed in large and small scale mixing equipment. They can be mixed in a household cake mixer, a large scale Banbury Mixer, large and small paddle mixers, and the like.

The dry (anhydrous) solid mixture of is preferably in the form of an intimate mixture of the cephalosporin and the hydroxypolycarboxylic acid particles. Preferably, the cephalosporin and the hydroxypolycarboxylic acid are each in the form of ready dissolvable powders. Such powders may be termed as fine grain powders comparable to granular or powdery sugar. The degree of blending of these powders is not critical so long as the right proportions of each component is dissolved in the body of water that is used in forming the solution comprising the cephalosporin and the hydroxypolycarboxylic acid. The key to blending and aliquoting the blend is to assure that the proper concentration of each component is present in the aliquot when the aliquot is dissolved in a common body of water.

The dry solid mixture may be dissolved in a small concentration of water, for example, an amount of water sufficient to dissolve all of the components of the dry mixture. This solution can be a concentrate of the cephalosporin and is used as a vehicle for supplying the ingredients of the dry solid mixture of the invention in the water feed of the animals.

EXAMPLE 1

The following anhydrous cephalosporin and hydroxylatedpolycarboxylic acid mixtures were formed without sweeteners and flavorings by addition to clear plastic bags and by working of the bags. The mixtures were added to water in the amounts noted and the conditions of dissolution are noted, as well as the resultant pH or the formed solution.

| Choice of Cephalosporin and amount | Choice of polyhydroxylated-polycarboxylic acid and amount | Amount of water | Comments |
|---|---|---|---|
| Cefadroxil 1 gram | Citric Acid 3 grams | 25 cc. | Formed a clear yellow solution within 2 minutes having a pH of about 3. |
| Cephradine 1 gram | Citric Acid 3.5 grams | 25 cc. | Formed a clear yellow solution in 15 minutes having a pH of about 3. |
| Cephaloridine 1 gram | Citric Acid 3 grams | 25 cc. | Formed a clear solution in 8 minutes that has a pH of about 3. |
| Cefaclor 0.1 gram | Citric Acid 0.3 gram | 2.5 cc. | Formed a solution in 12 minutes that has a pH of 2.8. |
| Cephalexin 5 grams | Citric Acid 10 grams | 50 cc. | Formed a clear yellow solution in 5 minutes that has a pH of 3.3. |

EXAMPLE 2

A flavored and sweetened formulation of the invention is made by thoroughly mixing 1 kg. of cephalexin monohydrate, 227 gms of Nutrasweet® Aspartame sweetener, 3 kg. of citric acid and 30 gms of strawberry flavoring. This anhydrous mixture is rapidly dissolved in water to a concentration of 128 grams of cephalexin per gallon of demineralized water to form a solution having a pH of about 3.5. A comparable solution is formed by substituting an equal weight amount of tartaric acid for the citric acid.

EXAMPLE 3

Three rooms of 500—10 kg 3 week old pigs were fed water with either (i) a solution of cephalexin monohydrate mixed with citric acid (made according to Example 3 using 125 grams of cephalexin monohydrate and 375 grams of citric acid, per gallon of water, exclusive of the Nutrasweet® Aspartame sweetener and the strawberry flavoring), (ii) cephalexin monohydrate mixed with hydrochloric acid (made by adding 40 cc of concentrated hydrochloric acid per gallon of water, to which is added with stirring, 125 grams of cephalexin monohydrate), or (iii) nothing added. Water consumption rates were measured in the three rooms. The measurement period was 7 days. Details of the experiment are set forth in the following table.

| Groups | Duration of Study | Gallons of H₂O consumed per day | Concentration of ceflexin in the drinking water | Effective cephalexin dose per kg of pig |
| --- | --- | --- | --- | --- |
| Citric acid and cephalexin solution | 7 days | 110 | 1,000 mg per gallon | 22 mg/kg |
| Hydrochloric acid and cephalexin solution | 7 days | 92 | 1,000 mg per gallon | 18.40 mg/kg |
| Non-treated control group | 7 days | 122 | 0 mg | 0 mg/kg |

It was found that the citric acid and cephalexin group showed increased consumption over the hydrochloric acid and cephalexin group. The highest consumption of water was in the non-treated group.

EXAMPLE 4

The following experiment exhibits the effect of adding artificial sweetener to the citric acid and cephalexin mixture. The same protocol as employed in example 3 above was used in this experiment except that where the Nutrasweet® Aspartame artificial sweetener was added to the anhydrous mixture, it was present in the relative concentration to cephalexin as set forth in Example 2 above. The object was to determine the effect of sweetener on the consumption of the citric acid and cephalexin mixture dissolved in water (as against the control group that was not supplied the cephalexin in the drinking water. Details of the experiment are set forth in the following table.

| Groups | Duration of Study | Gallons of H₂O consumed per day | Concentration of ceflexin in the drinking water | Effective cephalexin dose per kg of pig |
| --- | --- | --- | --- | --- |
| Citric acid and cephalexin solution plus Nutrasweet® | 7 days | 128 | 1,000 mg per gallon | 25.6 mg/kg |
| Hydrochloric acid and cephalexin solution | 7 days | 105 | 1,000 mg per gallon | 21 mg/kg |
| Non-treated control group | 7 days | 123 | 0 mg | 0 mg/kg |

The data shows that the addition of artificial sweetener increases the effective dose of cephalexin per unit weight of the pig.

EXAMPLE 5

This study documents the effectiveness of oral cephalexin/citric acid/Nutrasweet® Aspartame solution formed from a dry mixture of cephalexin monohydrate, citric acid and Nutrasweet® Aspartame, as described in Example 4 above, on the reduction and/or elimination of the Streptococcus state in 10 kg piglets. A farm was selected which was known to have problems with *Step suis* type 2 in its nursery pigs. The experiment involved two groups of 30 pigs, each group was in the same room, but in separate pens. Each pig was individually tagged and a tonsilar swab was done on day one and day seven. Cultures were run on all the swabs. One group was placed on cephalexin/citric acid/Nutrasweet® Aspartame in the drinking water (to a cephalexin concentration of 1,000 mg per gallon of water) for a daily treatment for the 7 days at 22 mg per kg of pig weight, and the other group served as a non-treated control. Details of the study are set forth in the following table.

| Group | Culture prior to medication | Culture day seven, post medication | Cephalexin dose per kg of pig weight | Average of gallons of water consumed per day. | Morbidity/mortality of the group during the study | Sensitivity of the organism |
| --- | --- | --- | --- | --- | --- | --- |
| Treated with cephalexin | 26 positive | 30 negative | 22 mg | 128 | 0 sick 0 died | sensitive to cephalexin |
| Control-untreated | 22 positive | 28 positive | 0 mg | 120 | 7 sick 1 died | sensitive to cephalexin |

The cephalexin provided via the mixture and solution of the invention was completely effective in eliminating the carrier state in the treated group of pigs compared to the untreated control.

EXAMPLE 6

The mixture and solution of the invention was tested in 100 to 200 pound pigs. The cephalexin/citric acid/Nutrasweet® Aspartame dry mixture described in Example 5 above was given to 1000 130 to 180 pound pigs with bacterial respiratory disease. The diagnostic laboratory confirmed that the pigs had *Pasturella multocida*, *Streptococcus suis Sp.* and *Actinobacillis pleuropneumonia* Type 7 pneumonia. All of the organisms showed sensitivity to cephalexin. Treatment was given for 5 days at an average of 5 mg of cephalexin per pound of the average pig weight. A 30 pig pen was used as a non-treated control group to measure the efficacy of the treatment. The 5 mg per pound treatment level is lower than recommended for dogs or humans but proved effective in this and follow-up trials. Details of the experiment are set forth in the table that immediately follows.

| Group | Treatment given | Mortality/morbidity 1 week prior to treatment | Mortality/morbidity for 2 weeks post treatment | Sensitivity results by the University Diagnostic Laboratory* | Duration of treatment | Clinical impression of the group by licensed veterinarian |
|---|---|---|---|---|---|---|
| Treatment of 970 pigs | cephalexin at 5 mg/lb. of pig, for 5 days | 220 sick 15 dead | 3 sick 1 dead | all bacteria were sensitive to cephalexin | 5 days | Rapid improvement in overcoming illness. 1 pig died on the first day and whole group was clinically better by the second day. |
| Control of 30 pigs | none | 6 sick 1 dead | 18 sick 3 dead | all bacteria were sensitive to cephalexin | 0 days | worsened steadily over the 2 weeks until treatment was given at the end of the second week |

*located in St. Paul, MN

EXAMPLE 7

A concentrated solution was formed by dissolving with stirring, 180 grams of cephalexin monohydrate, 540 grams of citric acid, and 40.86 gms of Nutrasweet® Aspartame in a gallon of water. Then 2.36 gallons of the concentrate were dissolved in 500 gallons of water and the modified water was used for treating four hundred pound steers and seven hundred 800 pound steers that were diagnosed with *Pasturella multocida* and *Pasturella heamolytica* pneumonia. The owner of the steers had lost 28 steers in a four day period prior to beginning the medication. The University Diagnostic Laboratory sensitivity report on both pathogens indicated that cephalosporins (particularly cephalexin) should be effective in treating the pneumonia. The cattle were daily fed 10 mg of cephalexin per average pound by controlling the treated water uptake, for 5 days. There was a general improvement of symptoms and appetite by 36 hours after treatment was started. Only two additional steers died and no relapse in disease was noted after the conclusion of the 5 day treatment period. Consumption of the mixture of cephalexin, citric acid and Nutrasweet® Aspartame was good indicating that the mixture was palatable to the animals.

We claim:

1. A dry solid mixture of a cephalosporin and a hydroxypolycarboxylic acid of the formula

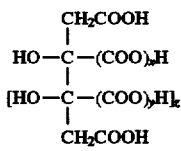

where x and y are 0 or 1 and z is 0 to 3, in the weight ratio of hydroxypolycarboxylic acid to cephalosporin of at least 1.8.

2. The dry solid mixture of claim 1 wherein the hydroxylatedpolycarboxylic acid is selected from the group of citric acid, tartaric acid, 2-hydroxy malonic acid, 2-hydroxyl n-butyl 1,2,4-tricarboxylic acid, glucaric acid, and 2-hydroxy n-butyl 1,3,4-tricarboxylic acid.

3. The dry solid mixture of claim 1 wherein the cephalosporin is selected from the group of cephamycins cefotetan and cefoxitin, cefazolin sodium, cephalexin, cephaloridine, cephaloglycin, cephalothin, cephapirin, cephradine, cephalothin, cefazolin, cephaloridione, cephapirin, cefadroxil, cefamanadole, cefoxitin, cefaclor, cefurotrime, cefoperazone, cefotaxime, ceftriaxone, ceftazidime, ceftizoxime, and moxalactam.

4. The dry solid mixture of claim 1 wherein the weight ratio of hydroxypolycarboxylic acid to cephalosporin is at least 2.5.

5. The dry solid mixture of claim 2 wherein the weight ratio of hydroxypolycarboxylic acid to cephalosporin is at least 2.5.

6. The dry solid mixture of claim 3 wherein the weight ratio of hydroxypolycarboxylic acid to cephalosporin is at least 2.5.

7. The dry solid mixture of claim 4 wherein the weight ratio of hydroxypolycarboxylic acid to cephalosporin is not greater than 10.

8. The dry solid mixture of claim 5 wherein the weight ratio of hydroxypolycarboxylic acid to cephalosporin is not greater than 10.

9. The dry solid mixture of claim 6 wherein the weight ratio of hydroxypolycarboxylic acid to cephalosporin is not greater than 10.

10. The dry solid mixture of claim 7 wherein the weight ratio of hydroxypolycarboxylic acid to cephalosporin is not greater than 10.

11. The dry solid mixture of claim 1 wherein the weight ratio of hydroxypolycarboxylic acid to cephalosporin is about 3.

12. The dry solid mixture of claim 2 wherein the weight ratio of hydroxypolycarboxylic acid to cephalosporin is about 3.

13. The dry solid mixture of claim 3 wherein the weight ratio of hydroxypolycarboxylic acid to cephalosporin is about 3.

14. The dry solid mixture of claim 1 wherein the cephalosporin is cephalexin.

15. The dry solid mixture of claim 2 wherein the cephalosporin is cephalexin.

16. The dry solid mixture of claim 3 wherein the cephalosporin is cephalexin.

17. The dry solid mixture of claim 4 wherein the cephalosporin is cephalexin.

18. The dry solid mixture of claim 5 wherein the cephalosporin is cephalexin.

19. The dry solid mixture of claim 6 wherein the cephalosporin is cephalexin.

20. The dry solid mixture of claim 7 wherein the cephalosporin is cephalexin.

21. The dry solid mixture of claim 8 wherein the cephalosporin is cephalexin.

22. The dry solid mixture of claim 9 wherein the cephalosporin is cephalexin.

23. The dry solid mixture of claim 10 wherein the cephalosporin is cephalexin.

24. The dry solid mixture of claim 11 wherein the cephalosporin is cephalexin.

25. The dry solid mixture of claim 12 wherein the cephalosporin is cephalexin.

26. The dry solid mixture of claim 13 wherein the cephalosporin is cephalexin.

27. The dry solid mixture of claim 14 wherein the hydroxypolycarboxylic acid is citric acid.

28. The dry solid mixture of claim 15 wherein the hydroxypolycarboxylic acid is citric acid.

29. The dry solid mixture of claim 16 wherein the hydroxypolycarboxylic acid is citric acid.

30. The dry solid mixture of claim 17 wherein the hydroxypolycarboxylic acid is citric acid.
31. The dry solid mixture of claim 18 wherein the hydroxypolycarboxylic acid is citric acid.
32. The dry solid mixture of claim 19 wherein the hydroxypolycarboxylic acid is citric acid.
33. The dry solid mixture of claim 20 wherein the hydroxypolycarboxylic acid is citric acid.
34. The dry solid mixture of claim 21 wherein the hydroxypolycarboxylic acid is citric acid.
35. The dry solid mixture of claim 22 wherein the hydroxypolycarboxylic acid is citric acid.
36. The dry solid mixture of claim 23 wherein the hydroxypolycarboxylic acid is citric acid.
37. The dry solid mixture of claim 24 wherein the hydroxypolycarboxylic acid is citric acid.
38. The dry solid mixture of claim 25 wherein the hydroxypolycarboxylic acid is citric acid.
39. The dry solid mixture of claim 26 wherein the hydroxypolycarboxylic acid is citric acid.
40. The dry solid mixture of claim 27 wherein a sweetener is present in the mixture.
41. The dry solid mixture of claim 28 whereto a sweetener is present in the mixture.
42. The dry solid mixture of claim 29 wherein a sweetener is present in the mixture.
43. The dry solid mixture of claim 30 wherein a sweetener is present in the mixture.
44. The dry solid mixture of claim 31 wherein a sweetener is present in the mixture.
45. The dry solid mixture of claim 32 wherein a sweetener is present in the mixture.
46. The dry solid mixture of claim 33 wherein a sweetener is present in the mixture.
47. The dry solid mixture of claim 34 wherein a sweetener is present in the mixture.
48. The dry solid mixture of claim 35 wherein a sweetener is present in the mixture.
49. The dry solid mixture of claim 36 wherein a sweetener is present in the mixture.
50. The dry solid mixture of claim 37 wherein a sweetener is present in the mixture.
51. The dry solid mixture of claim 38 wherein a sweetener is present in the mixture.
52. The dry solid mixture of claim 39 wherein a sweetener is present in the mixture.
53. The dry solid mixture of claim 40 wherein a flavoring is present in the mixture.
54. The dry solid mixture of claim 41 wherein a flavoring is present in the mixture.
55. The dry solid mixture of claim 42 wherein a flavoring is present in the mixture.
56. The dry solid mixture of claim 43 wherein a flavoring is present in the mixture.
57. The dry solid mixture of claim 44 wherein a flavoring is present in the mixture.
58. The dry solid mixture of claim 45 wherein a flavoring is present in the mixture.
59. The dry solid mixture of claim 46 wherein a flavoring is present in the mixture.
60. The dry solid mixture of claim 47 wherein a flavoring is present in the mixture.
61. The dry solid mixture of claim 48 wherein a flavoring is present in the mixture.
62. The dry solid mixture of claim 49 wherein a flavoring is present in the mixture.
63. The dry solid mixture of claim 50 wherein a flavoring is present in the mixture.
64. The dry solid mixture of claim 51 wherein a flavoring is present in the mixture.
65. The dry solid mixture of claim 52 wherein a flavoring is present in the mixture.

66. An aqueous solution comprising a palatable concentration of a cephalosporin and a hydroxypolycarboxylic acid of the formula

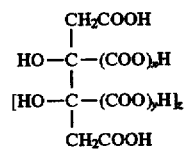

where x and y are 0 or 1 and z is 0 to 3 in the weight ratio of the hydroxypolycarboxylic acid to cephalosporin of at least about 1.8.
67. The aqueous solution of claim 66 wherein the weight ratio is at least about 2.5.
68. The aqueous solution of claim 66 wherein the weight ratio is not greater than about 10.
69. The aqueous solution of claim 68 wherein the weight ratio is not greater than about 10.
70. The aqueous solution of claim 66 wherein the hydroxypolycarboxylic acid is present in weight ratio to the cephalosporin of about 3 and the solution has a pH of about 3.0 to as high as about 4.0.
71. The aqueous solution of claim 66 wherein the hydroxypolycarboxylic acid is present in weight ratio to the cephalosporin of about 3 and the solution has a pH of about 3.0 to as high as about 4.0.
72. The aqueous solution of claim 67 wherein the hydroxypolycarboxylic acid is present in weight ratio to the cephalosporin of about 3 and the solution has a pH of about 3.0 to as high as about 4.0.
73. The aqueous solution of claim 68 wherein the hydroxypolycarboxylic acid is present in weight ratio to the cephalosporin of about 3 and the solution has a pH of about 3.0 to as high as about 4.0.
74. The aqueous solution of claim 69 wherein the hydroxypolycarboxylic acid is present in weight ratio to the cephalosporin of about 3 and the solution has a pH of about 3.0 to as high as about 4.0.
75. The aqueous solution of claim 66 wherein the hydroxypolycarboxylic acid is citric acid and the cephalosporin is cephalexin.
76. The aqueous solution of claim 66 wherein the hydroxypolycarboxylic acid is citric acid and the cephalosporin is cephalexin.
77. The aqueous solution of claim 67 wherein the hydroxypolycarboxylic acid is citric acid and the cephalosporin is cephalexin.
78. The aqueous solution of claim 68 wherein the hydroxypolycarboxylic acid is citric acid and the cephalosporin is cephalexin.
79. The aqueous solution of claim 69 wherein the hydroxypolycarboxylic acid is citric acid and the cephalosporin is cephalexin.
80. The aqueous solution of claim 70 wherein the hydroxypolycarboxylic acid is citric acid and the cephalosporin is cephalexin.
81. The aqueous solution of claim 71 wherein the hydroxypolycarboxylic acid is citric acid and the cephalosporin is cephalexin.
82. The aqueous solution of claim 72 wherein the hydroxypolycarboxylic acid is citric acid and the cephalosporin is cephalexin.
83. The aqueous solution of claim 73 wherein the hydroxypolycarboxylic acid is citric acid and the cephalosporin is cephalexin.
84. The aqueous solution of claim 74 wherein the hydroxypolycarboxylic acid is citric acid and the cephalosporin is cephalexin.
85. The aqueous solution of claim 66 in which there is provided a sweetener, and optionally, a flavoring.

86. The aqueous solution of claim 75 wherein there is provided a sweetener, and optionally, a flavoring.

87. The aqueous solution of claim 76 wherein there is provided a sweetener, and optionally, a flavoring.

88. The aqueous solution of claim 77 wherein there is provided a sweetener, and optionally, a flavoring.

89. The aqueous solution of claim 78 wherein there is provided a sweetener, and optionally, a flavoring.

90. The aqueous solution of claim 80 wherein there is provided a sweetener, and optionally, a flavoring.

91. A process for the treatment of a bacterial infection in an animal in need thereof which comprises orally administering to said animal an anti-bacterial effective amount of a cephalosporin which is in an aqueous solution comprising a hydroxypolycarboxylic acid and the cephalosporin in the weight ratio of at least 1.8 and the hydroxypolycarboxylic acid has the formula

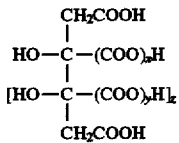

where x and y are 0 or 1 and z is 0 to 3.

92. The process of claim 91 wherein the weight ratio is at least 2.5.

93. The process of claim 92 wherein the weight ratio is not greater than 10.

94. The process of claim 93 wherein the weight ratio is about 3.

95. The process of claim 91 wherein the cephalosporin is cephalexin and the hydroxypolycarboxylic acid is citric acid.

96. The process of claim 92 wherein the cephalosporin is cephalexin and the hydroxypolycarboxylic acid is citric acid.

97. The process of claim 93 wherein the cephalosporin is cephalexin and the hydroxypolycarboxylic acid is citric acid.

98. The process of claim 94 wherein the cephalosporin is cephalexin and the hydroxypolycarboxylic acid is citric acid.

99. The process of claim 91 wherein there is provided a sweetener, and optionally, a flavoring in the solution.

100. The process of claim 92 wherein there is provided a sweetener, and optionally, a flavoring in the solution.

101. The process of claim 93 wherein there is provided a sweetener, and optionally, a flavoring in the solution.

102. The process of claim 94 wherein there is provided a sweetener, and optionally, a flavoring in the solution.

103. The process of claim 95 wherein there is provided a sweetener, and optionally, a flavoring in the solution.

104. The process of claim 96 wherein there is provided a sweetener, and optionally, a flavoring in the solution.

105. The process of claim 97 wherein there is provided a sweetener, and optionally, a flavoring in the solution.

106. The process of claim 98 wherein there is provided a sweetener, and optionally, a flavoring in the solution.

* * * * *